US00RE38417E

(19) United States
(12) Reissued Patent
Bergeron, Jr.

(10) Patent Number: US RE38,417 E
(45) Date of Reissued Patent: Feb. 3, 2004

(54) ANTI-NEOPLASTIC, ANTI-VIRAL OR ANTI-RETROVIRAL SPERMINE DERIVATIVES

(75) Inventor: Raymond J. Bergeron, Jr., Gainesville, FL (US)

(73) Assignee: University of Florida Research Foundation, Inc., Gainesville, FL (US)

(21) Appl. No.: 10/212,365

(22) Filed: Aug. 2, 2002

Related U.S. Patent Documents

Reissue of:
(64) Patent No.: 5,091,576
Issued: Feb. 25, 1992
Appl. No.: 07/210,520
Filed: Jun. 23, 1988

U.S. Applications:

(63) Continuation-in-part of application No. 07/066,227, filed on Jun. 25, 1987, now abandoned, which is a continuation-in-part of application No. 06/936,835, filed on Dec. 2, 1986, now abandoned.

(51) Int. Cl.[7] ..... C07C 211/14
(52) U.S. Cl. ..... 564/367; 564/361; 564/511; 564/512
(58) Field of Search ..... 564/511, 512, 564/367, 360

(56) References Cited

U.S. PATENT DOCUMENTS

| | | | | |
|---|---|---|---|---|
| 2,267,204 A | 12/1941 | Kyrides | ..... | 564/412 X |
| 2,279,294 A | 4/1942 | Hardman | ..... | 564/412 X |
| 2,638,450 A | 5/1953 | White et al. | ..... | 564/412 X |
| 2,687,348 A | 8/1954 | Kosmin | ..... | 564/412 X |
| 4,505,861 A | 3/1985 | Bergeron | ..... | 564/412 X |

FOREIGN PATENT DOCUMENTS

JP SHO.52-118405 10/1977

OTHER PUBLICATIONS

Glaser R and Gabbay E J, "Topography of Nucleic Acid Helices in Solutions. III. Interactions of Spermine and Spermine Derivatives with Polyadenylic–Polyuridylic and Polyinosinic–Polycytidylic Acid Helices," *Biopolymers* 6:243–254 (1968).

Clay R M et al., "Noncyclic Reference Ligands for Tetraaza Macrocycles. Synthesis and Therodynamic Properties of a Series of α, ω–Di–N–methylated Tetraaza Ligands and Their Copper (II) Complexes," *Inorganic Chemistry* 24(21):3330–3336 (1985).

Egami F et al, "Polyamines", *Chemical Abstracts* 88:104654 (1978).

*Primary Examiner*—Richard L. Raymond
(74) *Attorney, Agent, or Firm*—Hamilton, Brook, Smith & Reynolds, P.C.

(57) ABSTRACT

The present invention relates to anti-neoplastic and anti-psoriasis pharmaceutical compositions and methods of treatment and to insecticidal compositions and methods of controlling the growth of insects.

14 Claims, No Drawings

ANTI-NEOPLASTIC, ANTI-VIRAL OR ANTI-RETROVIRAL SPERMINE DERIVATIVES

Matter enclosed in heavy brackets [ ] appears in the original patent but forms no part of this reissue specification; matter printed in italics indicates the additions made by reissue.

RELATED APPLICATIONS

This *is a reissue of application Ser. No. 07/210,520, filed Jun. 23, 1988, now U.S. Pat. No. 5,091,576, which* is a continuation-in-part of application Ser. No. 066,227, filed Jun. 25, 1987, now abandoned, which is a continuation-in-part application of application Ser. No. 936,835, filed Dec. 2, 1986*, now abandoned.*

BACKGROUND OF THE INVENTION

This invention was made with U.S. Government support under Grant NCDDG-CA37606, awarded by the National Cancer Institute. The U.S. Government has certain rights in this invention.

FIELD OF THE INVENTION

The present invention relates to anti-neoplastic and anti-psoriasis pharmaceutical compositions and methods of treatment and to insecticidal compositions and methods of controlling the growth of insects.

In recent years a great deal of attention has been focused on the polyamines, e.g., spermidine, norspermidine, homospermidine, 1,4-diaminobutane (putrescine), and spermine. These studies have been directed largely at the biological properties of the polyamines probably because of the role they play in proliferative processes. It was shown early on that the polyamine levels in dividing cells, e.g., cancer cells, are much higher than in resting cells. See Janne et al, A. Biochim. Biophys. Acta. 473, 241 (1978); Fillingame et al, Proc. Natl. Acad. Sci. U.S.A. 72: 4042 (1975); Metcalf et al, J. Am. Chem. Soc. 100:2551 (1978); Flink et al, Nature (London) 253:62 (1975); and Pegg et al, Polyamine Metabolism and Function, Am. J. Cell. Physiol. 243:212–221 (1982).

macromolecules such as nucleic acids by anion neutralization. See Dkystra et al, Science, 149:48 (1965); Russell et al, Polyamines as Biochemical Markers of Normal and Malignant Growth (Raven, New York, 1978); Hirschfield et al, J. Bacteriol., 101:725 (1970); Morris et al, ibid, p. 731; Whitney et al, ibid, 134:214 (1978); Hafner et al, J. Biol. Chem., 254:12419 (1979); Cohn et al, J. Bacteriol. 134:208 (1978); Pohjatipelto et al, Nature (London), 293:475 (1981); Mamont et al, Biochem. Biophys. Res. Commun. 81:58 (1978); Bloomfield et al, Polyamines in Biology and Medicine (D. R. Morris and L. J. Morton, Eds.—Dekker, New York, 1981) pp. 183–205; Gosule et al, Nature, 259:333 (1976); Gabbay et al, Ann. N.Y. Acad. Sci., 171:810 (1970); Suwalsky et al, J. Mol. Biol., 42:363 (1969) and Liquori et al, J. Mol. Biol., 24:113 (1968).

However, regardless of the reason for increased polyamine levels the phenomenon can be and has been exploited in chemotherapy. See Sjoerdsma et al, Butterworths Int. Med. Rev.: Clin. Pharmacol. Ther. 35:287 (1984); Israel et al, J. Med. Chem., 16:1 (1973); Morris et al, Polyamines in Biology and Medicine; Dekker, New York, p. 223 (1981) and Wang et al, Biochem. Biophys. Res. Commun., 94:85 (1980).

It is an object of the present invention to provide novel anti-neoplastic, -viral and -retroviral compounds, pharmaceutical compositions and methods of treatment.

SUMMARY OF THE INVENTION

The foregoing and other objects are realized by the present invention, one embodiment of which is a pharmaceutical composition comprising an anti-neoplastic, anti-viral, anti-retroviral or anti-psoriasis effective amount of a compound, having one of the formulae:

(I)

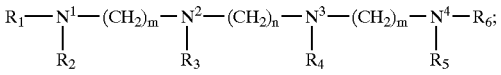

(II)

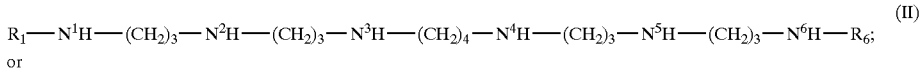

or (III)

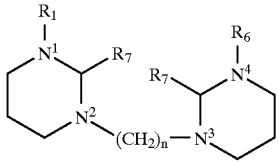

Several lines of evidence indicate that polyamines, particularly spermidine, are required for cell proliferation: (i) they are found in greater amounts in growing than in non-growing tissues; (ii) prokaryotic and eukaryotic mutants deficient in polyamine biosynthesis are auxotrophic for polyamines; and (iii) inhibitors specific for polyamine biosynthesis also inhibit cell growth. Despite this evidence, the precise biological role of polyamines in cell proliferation is uncertain. It has been suggested that polyamines, by virtue of their charged nature under physiological conditions and their conformational flexibility, might serve to stabilize Wherein:

$R_1$ and $R_6$ may be the same or different and are H, alkyl or aralkyl having from 1 to 12 carbon atoms, $R_2$–$R_5$ may be the same or different and are H, $R_1$ or $R_6$;

$R_7$ is H, alkyl, aryl or aralkyl having from 1 to 12 carbon atoms;

m is an integer from 3 to 6, inclusive, n is an integer from 3 to 6, inclusive; and a pharmaceutically acceptable carrier therefor.

An additional embodiment of the invention comprises a method of treating a human or non-human animal in need of anti-neoplastic, anti-viral, anti-retroviral or anti-psoriasis therapy comprising administering to the animal an anti-neoplastic, anti-viral, anti-retroviral or anti-psoriasis effective amount of a compound having one of the above formulae.

A further embodiment of the invention comprises a compound having the formula:

(I)

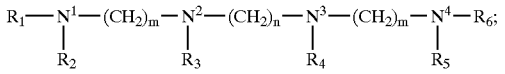

Wherein:

$R_1$–$R_6$ may be the same or different and are methyl, propyl, butyl, pentyl, benzyl or β,β,β-trifluoroethyl;

m is an integer from 3 to 6, inclusive;

n is an integer from 3 to 6, inclusive.

A further embodiment of the invention comprises a compound having the formula:

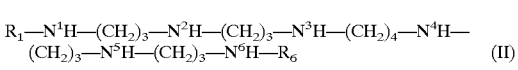

(II)

Wherein:

$R_1$ and $R_6$ may be the same or different and are alkyl or aralkyl having from 1 to 12 carbon atoms.

A final embodiment of the invention comprises a compound having the formula:

(III)

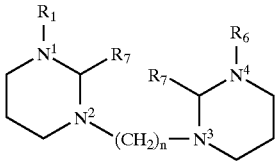

Wherein:

$R_1$ and $R_6$ may be the same or different and are alkyl or aralkyl having from 1 to 12 carbon atoms;

$R_7$ is H, alkyl, aralkyl or aryl having from 1 to 12 carbon atoms;

n is an integer from 3 to 6, inclusive.

DETAILED DESCRIPTION OF THE INVENTION

In compounds of the invention, $R_1$ and $R_6$ are preferably methyl, ethyl, propyl, benzyl, etc., it being understood that the term "aralkyl" is intended to embrace any aromatic group the chemical and physical properties of which do not adversely affect the efficacy and safety of the compound for therapeutic applications. Preferred, however, are the hydrocarbyl aralkyl groups, i.e., comprised only of C and H atoms.

$R_2$–$R_5$ preferably are H, methyl, ethyl, propyl or benzyl.

Compounds of formula (I) are preferably synthesized by first forming a sulfonamide of the polyamine at all of the amino nitrogens (1) to activate the primary amines for monoalkylation, and (2) to protect any secondary nitrogens from alkylation. Suitable sulfonating agents include alkyl, aryl and arylalkyl sulfonating agents of the general structure $RSO_2X$ wherein R is alkyl, aryl or arylalkyl and X is a leaving group, e.g., $Cl^-$, $Br^-$, etc. The sulfonation is accomplished by reacting the polyamine with 1.0 equivalent of sulfonating agent per nitrogen in the presence of a base, e.g., tertiary amine or a hydroxide. The reaction is best accomplished using aqueous sodium hydroxide as the base and p-toluenesulfonyl chloride (TsCl) a the sulfonating agent in a biphasic solvent systems consisting of an organic solvent, e.g., methylene chloride and water. The sulfonating agent is added in methylene chloride to an aqueous solution of the amine and sodium hydroxide and the reaction proceeds according to the following equation, using spermine as the base compound:

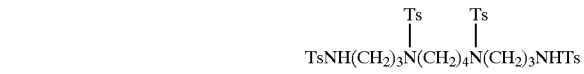

Where: Ts=p-toluenesulfonyl.

After purification the sulfonamide is next alkylated. The alkylations involve formation of N-anions on the primary amino sulfonamides with a base such as NaH followed by reaction of the N-anion with an alkylating agent RX wherein R is as defined above and X is a leaving group such as $I^-$, $Cl^-$, $Br^-$, p-$CH_3C_6H_4SO_3^-$, $CH_3SO_3^-$.

The alkylation can be carried out in a variety of dipolar aprotic solvents, preferably, N, N-dimethylformamide (DMF). The reaction proceeds according to the following equation:

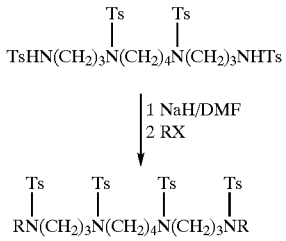

After alkylation of the sulfonamide, the sulfonyl protecting groups are next removed under reducing conditions. Although a variety of standard reducing conditions can be utilized ($LiAlH_4$, $Li/NH_3$, catalytic reduction), Na and $NH_3$ function optimally. The reduction proceeds according to the following equation:

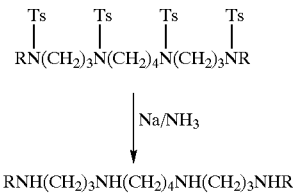

The compounds are isolated as the free amines and then may be converted to and utilized as the corresponding hydrochloride salts by treatment with concentrated HCl. However, they may also be used as salts with any pharmaceutically acceptable acid, e.g., HBr, $CH_3CO_2H$, $CH_3SO_3H$, etc.

Compounds of formula (II) are preferably prepared by the mono-alkylation of tetratosyl spermine at each of the primary nitrogens by reagents such as N-alkyl-N-(3-chloropropyl)-p-toluenesulfonamide. Terminal alkylation of spermine is carried out using the conditions employed for preparing compound (I) according to the following scheme:

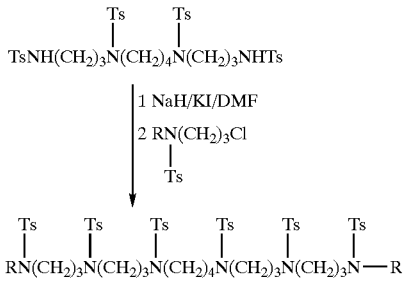

The alkylating agent is formed by treatment of N-alkyl-p-toluenesulfonamide with excess 1,3 dichloropropane under the aforementioned conditions according to the following scheme:

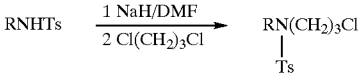

After purification of the dialkylated hexatosylated hexaamine, the sulfonyl protecting groups are removed reductively with sodium in liquid ammonia and THF as follows:

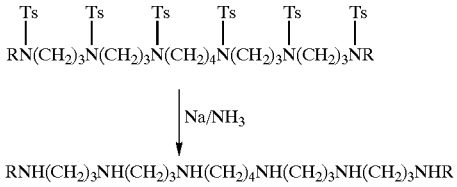

The final product is isolated as the free amine and may be converted to the hydrochloride salt.

Compounds of formula (III) may be prepared by reacting a tetraamine of formula (I) in which $R_2$—$R_5$=H and $R_1$,$R_6$=alkyl or aralkyl with two equivalents of an aldehyde $R_7$CHO, wherein $R_7$=H, alkyl or aralkyl.

Specifically, to $N^1$,$N^4$-diethylspermine tetrahydrochloride is added aqueous NaOH and formalin (two equivalents) to generate the bis-hexahydropyrimidine as follows:

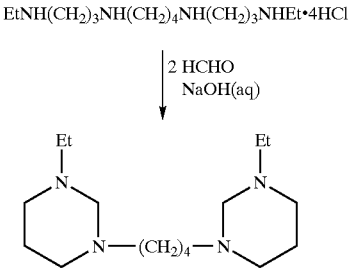

The invention is illustrated by the following non-limiting examples.

EXAMPLE 1

Preparation of $N^1$,$N^4$-diethylspermine $N^1$,$N^2$,$N^3$,$N^4$-Tetra-p-tosylspermine. To spermine tetrahydrochloride (4.53 g, 13.0 mmol) and 10% aqueous NaOH (200 mL, 132 mmol) at 0° is added dropwise p-toluenesulfonyl chloride (9.98 g, 52.3 mmol) in $CH_2Cl_2$ with rapid stirring. After 1 hr the mixture is allowed to warm to room temperature and to stir for 2 days. The organic phase is separated and washed with 0.5N HCl, $H_2O$, and brine, dried over $Na_2SO_4$ and purified on silica gel (450 g, 3% MeOH/$CHCl_3$) to give 9.69 g, 91% yield of tetratosylspermine.

NMR ($CDCl_3$)δ7.2–7.9 (m, 16H), 5.34 (t, 2H, J=7), 2.9–3.3 (m, 12H), 2.43 (s, 12H), 1.5–2.0 (m, 8H).

$N^1$,$N^4$-Diethyl-$N^1$,$N^2$,$N^3$,$N^4$-Tetra-p-tosylspermine. To the tetratosylspermine prepared above (1.75 g, 2.14 mmol) in dry DMF (12 mL) was cautiously added 80% sodium hydride (0.25 g, 8.33 mmol) and then ethyl iodide (1.0 mL, 12.5 mmol). After heating under nitrogen (10 h, 55°), the mixture was quenched with ice water and extracted with chloroform (3 x). The organic phase was washed with 5% $Na_2SO_3$, 5% NaOH, 1N HCl, and water, then dried with $Na_2SO_4$. Removal of DMF by flash distillation and purification of the crude product on silica gel (4% EtOH/$CHCl_3$) product 1.63 g (87%) of the desired product. NMR ($CDCl_3$) δ7.2–7.8 (m, 16H), 3.03–3.3 (m, 16H), 2.43 (s, 12H),1.5–2.1 (m, 8H), 1.08 (t, 6H, J=7). Anal. Calcd. for $C_{24}H_{58}N_4O_8S_4$; C, 57.64; H, 6.68; N, 6.40. Found: C, 57.69; H, 6.74; N, 6.20.

$N^1$,$N^4$-diethylspermine (DES). Into a solution of the $N^1$,$N^4$-diethyl-$N^1$,$N^2$,$N^3$,$N^4$-tetratosylspermine prepared above (2.78 g, 3.18 mmoles) in dry, distilled THF (200 mL) at −78° C. was condensed 300 mL $NH_3$, using a dry ice condenser. Sodium spheres (3.0 g, 0.13 mol) were then added in small portions and the reaction mixture was stirred at −78° C. for 4 h. The reaction mixture was allowed to warm to room temperature overnight and the $NH_3$ boiled off. Diethyl ether was added to the mixture. Ethanol was then cautiously added, then $H_2O$ was added to finally quench the reaction. The solvents were evaporated and the product extracted with diethyl ether and then chloroform. The extracts were dried over $Na_2SO_4$, filtered and the extracts concentrated. The resultant liquid was distilled in a Kugelrohr apparatus (150° C., 0.1 mm). Concentrated hydrochloric acid was added to an ether/ethanol (1:1) solution of the distillate to form the hydrochloride salt, which was recrystallized from hot aqueous ethanol to give 790 mg (63%) DES. NMR ($D_2O$)δ1.4 (t, 6H); 1.9 (m, 4H); 2.25 (m, 4H); 3.25 (m, 16H); 4.80 (s, HOD, reference).

The following protocols were followed to determine the $IC_{50}$ values for DES against cultured L1210 cells, Daudi cells and HL-60 cells.

Cell Culture.

Murine L1210 leukemia cells, human Burkitt lymphoma cells (Daudi) and human promyelocytic leukemia cells (HL-60) were maintained in logarithmic growth as suspension cultures in RPMI-1640 medium containing 2% 4-(1-hydroxyethyl)-1-piperazineethanesulfonic acid/ 3-(N-morpholino)propanesulfonic acid, 100 μM aminoguanidine, and 10% fetal bovine serum. Cells were grown in 25 sq cm tissue culture flasks in a total volume of 10 mL under a humidified 5% $CO_2$ atmosphere at 37° C.

The cells were treated while in logarithmic growth (L1210 cells $0.3\times10^5$ cells/mL; Daudi and HL-60 $1\times10^5$ cells/mL) with the polyamine derivatives diluted in sterile water and filtered through a 0.2 micron filter immediately prior to use. Following a 48 h incubation with L1210 cells and a 72 h incubation with Daudi or HL-60 cells, L1210 cells were reseeded at $0.3\times10^5$ cells/mL, Daudi and HL-60 cells were reseeded at $1\times10^5$ cells/mL and all cells were incubated in the presence of the polyamine derivative for an additional 48 h or 72 h.

Cell samples at the indicated time periods were removed for counting. Cell number was determined by electronic particle counting and confirmed periodically with hemocytometer measurements. Cell viability was assessed by trypan blue dye exclusion.

The percentage of control growth was determined as follows:

$$\%\text{ of control growth} = \frac{\text{Final treated cell no.} - \text{initial inoculum}}{\text{Final untreated cell no.} - \text{initial inoculum}} \times 100$$

The $IC_{50}$ is defined as the concentration of compound necessary to reduce cell growth to 50% of control growth.

The results are set forth in Tables 1 and 2.

TABLE 1

| | L1210 Cells | |
|---|---|---|
| | 48 H $IC_{50}$ | 96 H $IC_{50}$ |
| DES | 10 μM | 0.10 μM |

TABLE 2

| | Daudi Cells | | HL-60 Cells | |
|---|---|---|---|---|
| | 72 H $IC_{50}$ | 144 H $IC_{50}$ | 72 H $IC_{50}$ | 144 H $IC_{50}$ |
| DES | >40 μM | 0.5 μM | 10 μM | 0.3 μM |

Animal Studies.

The murine L1210 leukemia cells were maintained in DBA/2J mice. L1210 cells, from a single mouse which was injected i.p. with $10^6$ cells 5 days earlier, were harvested and diluted with cold saline so that there were $10^5$ or $10^6$ cells in 0.25 cc. For each study, mice were injected i.p. with $10^6$ L1210 cells or $10^5$ L1210 cells (See Table 3) on day 0. The polyamine analogues were diluted in sterile saline within 24 h of use and the unused portions stored at 5° C.

DES was administered by i.p. injection 15 mg/kg or 20 mg/kg every 8 h for 3 days (days 1–3), 4 days (days 1–4), or 6 days (days 1–6) (See Table 3).

Mice which were treated with saline injections served as controls.

The parameter used for treatment evaluation was mean survival time.

(Percent increased life span, % ILS).

$$\%\ ILS = \frac{\text{mean survival time treated animals} - \text{mean survival time controls}}{\text{mean survival controls}} \times 100$$

The murine Lewis lung carcinoma was maintained as s.c. tumor in C57B1/6 mice. The line was propagated every 14 days. A 2–4 mm fragment of s.c. donor tumor was implanted s.c. in the auxiliary region with a puncture in the inguinal region on day 0.

DES was administered by i.p. injection 20 mg/kg every 8 h for 5 days beginning on day 5 (days 5–9). Equal numbers of mice treated with saline injections served as controls. The parameter used for treatment evaluation was mean survival time (% ILS).

The parameters of the animal tests and results are set forth below in Tables 3 and 4.

TABLE 3

Evaluation of DES in DBA/2J Male Mice with L1210 Leukemia (i.p.)

| DES | Dosing Schedule | No. Animals | Day of Death | Mean Survival SD | % ILS |
|---|---|---|---|---|---|
| (1)[a] | 15 mg/kg q12 hr days 1–6 | 6 | 14, 14, 14.5, 15, 15, 17 | 14.9 ± 1.3 | 55 |
| | Control | 7 | 8.5, 9.5, 9.5, 9.5, 10, 10, 10 | 9.6 ± 0.5 | 0 |
| (2)[b] | 20 mg/kg q8 hr days 1–3 | 4 | 13.5, 14, 14, 14.5 | 14.1 ± 0.5 | 57 |
| | Control | 4 | 8.5, 8.5, 9, 10 | 9.0 ± 0.5 | 0 |
| (3)[b] | 20 mg/kg q8 hr days 1–4 | 10 | 14, 14, 15, 15, 16, 17, 18, 20, 21, 31 | 16.7 ± 2.6 | 90 |
| | Control | 9 | 8, 8, 9, 9, 9, 9, 9, 9, 10 | 8.8 ± 0.4 | 0 |
| (4)[a] | 15 mg/kg q8 hr days 1–6 | 8 | 8, 20, 22.5, 24.5, 28.5, 60[d], 60[d], 60[d] | 27.8 ± 19.5 | 302 |
| | Control | 6 | 8.5, 9.5, 10, 10, 10.5, 10.5 | 9.8 ± 0.7 | 0 |

[a]Mice injected with $10^5$ L1210 cells i.p. on day 0.
[b]Mice injected with $10^6$ L1210 cells i.p. on day 0.
[c]Death of animal not included in statistics . . . greater or less than Mean Survival 2 × (S.D.).
[d]Experiment ended at 60 days. Animal survival evaluated on the day, however, these animals were alive with no sign of tumor.

TABLE 4

Evaluation of $N^1$, $N^4$-Di-ethylspermine (DES) in C57B1/6J Male Mice with Lewis Lung Carcinoma (s.c.)

| Drug | Dose (mg/kg) | Schedule | Survival Values (Days) Mean ± S.D. | % ILS |
|---|---|---|---|---|
| DES | 20 (i.p.) | Every 8 hr, days 5–9 | 43.7 ± 7.1 | 24 |
| Control (Saline) | — | — | 35.2 ± 2.6 | 0 |

The foregoing test results unequivocally establish the effectiveness of the composition of the invention as an anti-neoplastic agent.

EXAMPLE 2

N-Ethyl-N-(3-chloropropyl)-p-toluenesulfonamide. To N-ethyl-p-toluenesulfonamide (5.01 g, 0.0251 mol) in DMF (50 mL) in a dry flask is added sodium hydride (80% in oil, 0.93 g, 0.031 mol). After gas evolution subsides, 1,3-dichloropropane (22.48 g, 0.199 mol) is added. The mixture is heated at 53° C. for 10 h then cooled and poured into ice water (300 mL), which is extracted twice with ether. The combined extracts are washed with 1% sodium bisulfite, water (3×), and brine. Removal of solvent by rotary evaporation then Kugelrohr distillation gives crude product, which is chromatographed on silica gel (30% hexane/$CHCl_3$) to furnish 2.91 g product (42%) NMR ($CDCl_3$)δ1.15 (t, 3H), 1.9–2.2 (m, 2H), 2.44 (s, 3H), 3.11–3.35 (m, 4H), 3.6 (t, 2H), 7.3 (d, 2H). 3,7,11,16,20,24-Hexa(p-toluenesulfonyl)3,7,11,16,20,24-hexaazahexacosane. To tetra(p-toluenesulfonyl) spermine (1.82 g, 2.22 mmol) in dry DMF (10 mL) is added sodium hydride (80% in oil, 0.21 g, 7.0 mmol) and potassium iodide (53 g, 0.32 mmol). After 30 minutes, N-ethyl-N-(3-chloropropyl)-p-toluenesulfonamide (2.9 g, 10.5 mmol) in DMF (10 mL) is introduced and the mixture is stirred for 20 h at room temperature then heated at 40°–50° C. for 2 h. The cooled reaction mixture is poured into ice-cold 5% NaOH (100 mL), which is extracted with $CHCl_3$ (3×). A water wash, then solvent removal (rotovap then Kugelrohr distillation) yields crude hexatosylamide. Silica gel chromatography (1% EtOH/$CHCl_3$) affords 1.73 g of product (60%). NMRδ1.08 (t, 6H), 1.45–2.10 (m, 12H), 2.34 (s, 18H), 2.96–3.37 (m, 24H), 7.2–7.8 (m, 24H).

1,20-Bis(N-ethylamino)-4,8,13,17-tetraazaeicosane. A solution of the preceding compound (0.79 g, 0.61 mmol) in distilled THF (45 mL) is added to a dry 500 mL 3-necked flask, equipped with a dry ice condenser and 2 stoppers. The solution is cooled to about −40° C., and ammonia gas (200 mL), after passing through NaOH, is condensed. Sodium spheres (0.99, 43 mmol), which are rinsed in hexane (2×) and cut in half, are added cautiously. After maintaining the cold temperature for 4–5 h, ammonia gas is allowed to evaporate under a stream of nitrogen. To the residue at 0° C. is carefully added excess, absolute ethanol, and the mixture is concentrated. Sodium hydroxide (10%, 15 mL) is then added, and extraction with chloroform (10×20 mL), while saturating the aqueous layer with salt, gives crude free amine. Bulb-to-bulb distillation, up to 160° C./0.005 mm, furnishes 0.216 g free hexaamine, which is dissolved in ethanol and treated with 0.5 mL concentrated HCl. After solvent removal, the solid is recrystallized from 17% aqueous ethanol (120 mL) and washed with cold, absolute EtOH (2×3 mL) to afford 0.131 g of crystalline product (35%). 300 MHz NMR ($D_2O$) δ1.31 (t, 6H), 1.74–1.84 (m, 4H), 2.05–2.19 (m, 8H), 3.07–3.25 (m, 24H). Anal. calcd. for $C_{20}H_{54}Cl_6N_6$: C, 40.62; H, 9.20; N 14.21. Found: C, 40.73; H, 9.22; N, 14.22.

EXAMPLE 3

Bis(3-ethyl-1-hexahydropyrimidyl)-1,4-butane. To $N^1$,$N^4$-diethylspermine.4HCl (36.1 mg, 0.0893 mmol) in 0.17M NaOH (2.0 mL, 0.34 mmol) at 0° is added formalin (15 μL, 0.20 mmol). The solution is stirred at room temperature for 3 h, then 10% NaOH (4 mL) and brine (4 mL) are added. Extraction with $CH_2Cl_2$ (4×25 mL) and drying the extracts with $Na_2SO_4$ gives crude product. Column chromatography (silica gel, 2% concentrated $NH_4OH$/$CH_3OH$) furnishes 22 mg (88% yield) of the bis-hexahydropyrimidine. NMR ($CDCl_3$)δ1.10 (t, 6H), 1.4–1.9 (m, 8H), 2.32–2.65 (m, 16H), 3.15 (s, 4H).

EXAMPLE 4

The $IC_{50}$ values for several compounds according to the invention were determines as in Examples 1 and 2. The results are set forth in Table 5.

TABLE 5

L-1210 Cells [$IC_{50}$]

| | Compound | 48 hrs. | 96 hrs. |
|---|---|---|---|
| Formula I | $R_1 = R_6$ = methyl<br>m = 3<br>n = 4<br>$R_2 = R_3 = R_4 = R_5$ = H | 60% CG<br>100 μM | 0.75 μM |
| Formula I | $R_1 = R_6$ = propyl<br>m = 3<br>n = 4<br>$R_2 = R_3 = R_4 = R_5$ = H | 3 μM | 0.2 μM |
| Formula I | $R_1 = R_2 = R_5 = R_6$ = ethyl<br>$R_3 = R_4$ = H<br>m = 3<br>n = 4 | 80% CG<br>25 μM | 5 μM |
| Formula I | $R_2 = R_3 = R_4 = R_6$ = ethyl<br>$R_2 = R_5$ = H<br>m = 3<br>n = 4 | 100 μM | 3 μM |
| Formula II | $R_1 = R_6$ = ethyl | 50 μM | 0.5 μM |

EXAMPLE 5

The % ILS value for various dosages of $N^1$, $N^4$-diethylhomospermine were determined according to the procedure of Examples 1 and 2. The results are set forth in Table 6.

TABLE 6

L1210 i.p. Leukemia in DBA/2J female mice given $10^5$ cells on day 0.

| No. | Dosing Schedule | # Animals | Day of Death | Mean Survival + S.D. (days) | ILS (%) |
|---|---|---|---|---|---|
| 1. | 2.5 mg/kg q8 hr days 1–6 (i.p.) | 5 | 20.5, 32 23, 22, $60^d$ | 31.5 ± 16.6 | 242 |
| | Control | | | 9.2 ± 0.3 | |
| 2. | 5 mg/kg q8 hr days 1–6 (i.p.) | 10 | 25.9 × $60^d$ | 56.5 ± 11.1 | 524 |
| | Control | | | 9.1 ± 0.6 | |
| 3. | 10 mg/kg q12 hr days 1–6 (i.p.) | 6 | 31.5 × $60^d$ | 55.2 ± 11.8 | 441 |
| | Control | | | 10.2 + 1.1 | |

TABLE 6-continued

| | | | | | |
|---|---|---|---|---|---|
| | L1210 i.p. Leukemia in DBA/2J female mice given $10^5$ cells on day 0. | | | | |
| No. | Dosing Schedule | # Animals | Day of Death | Mean Survival + S.D. (days) | ILS (%) |
| 4. | 10 mg/kg once daily days (1–6 (i.p.) | 5 | 12, 17, 24, 24, 27 | 20.8 ± 6.1 | 115 |
| | Control | | | 9.3 ± 0.4 | |
| 5. | 15 mg/kg once daily days (i.p.) | 5 | 21, 27, | 45.6 ± 19.8 | 390 |
| | Control | | | 9.3 ± 0.3 | |

[a]Experiment ended at 60 days. Animal survival evaluated on this day, however, these animals were alive with no size of tumor.

Unexpectedly, and for reasons as not yet understood, the compounds of the invention have been found to be effective anti-viral, and most surprisingly, anti-retroviral agents.

The development of compounds useful for the prophylaxis and therapy of viral disease has presented more difficult problems than those encountered in the search for drugs effective in disorders produced by other microorganisms. This is primarily because, in contrast to most other infectious agents, viruses are obligate intracellular parasites that require the active participation of the metabolic processes of the invaded cell. Thus, agents that may inhibit or cause the death of viruses are also very likely to injure the host cells that harbor them. Although the search for substances that might be of use in the management of viral infections has been long and intensive, very few agents have been found to have clinical applicability. Indeed, even these have exhibited very narrow activity, limited to one or only a few specific viruses.

The retroviruses have presented an even greater challenge due to their even more complex intracellular metabolic activity.

The following examples illustrate the utilization of the compounds of the present invention as anti-retrovirus agents.

EXAMPLE 6

Embryonic chicken fibroblasts were grown to near confluence in cell culture media. The fibroblasts were next exposed to avian sarcoma virus for five hours. The cells were next washed with buffer to remove excess virus. The virus infected cells were then treated with 10 $\mu$M or 100 $\mu$M, $N^1$,$N^4$-diethylspermine, (DES), culture media for 18 hours. The cell culture media was next removed and the cells were overlaid with soft agar growth media. The cells were then allowed to grow at 37° C. for 6–8 days. The culture plates were evaluated for foci (transformed cells) utilizing an inverted microscope. The results of these measurements are indicated below.

TABLE 7

| NUMBER OF FOCI AT | 6-DAYS | 8-DAYS |
|---|---|---|
| CONTROL (ASV + FIBROBLASTS) | 300 | 300 |
| ASV + FIBROBLASTS + 10 $\mu$M DES | 20 | 300 |
| ASV + FIBROBLASTS + 100 $\mu$M DES | 0 | 110 |

In a second experiment the virus was first treated with DES at 10 $\mu$M or 100 $\mu$M for three hours and then added to the fibroblast monolayer for 18 hours at 37° C. The excess virus was then removed by washing and the monolayer overlaid with soft agar culture media. The plates were allowed to incubate at 37° C. for 8 days and the plates were examined for foci. The results are indicated as follows.

TABLE 8

| | NUMBER OF FOCI AT 8 DAYS |
|---|---|
| ASV + FIBROBLASTS (CONTROL) | 300 |
| ASV + FIBROBLASTS + 10 $\mu$M DES | 200 |
| ASV + FIBROBLASTS + 100 $\mu$M DES | 16 |

Inasmuch as the compounds described herein are anti-proliferation agents, they are also useful as anti-psoriasis agents. The following example illustrates the transdermal penetration characteristics of the compounds of the invention.

EXAMPLE 7

Hairless mice were sacrificed by cervical dislocation and their skin removed. The skin was denuded of fatty tissue and stretched over a drug diffusion cell. The diffusion cell contained a phosphate receptor phase at pH 7.4. The donor phase contained the drug DES dissolved in glycine buffer at pH 8.0 at a concentration of 10 mg/mL. Samples of the receptor phase (3 mL) were taken at 48 hours. After each sample was withdrawn, an equal volume of fresh receptor phase was added back. The samples removed from the diffusion cell were assayed for polyamine utilizing a liquid chromatography-C-18 reverse system. The samples were first acidified with perchloric acid and then reacted with dansyl chloride to produce the corresponding dansylated polyamines. The experiment revealed that DES did indeed cross the skin at the dermal barrier.

For each of the utilities mentioned herein, the amount required of active agent and the frequency of its administration will vary with the identity of the agent concerned and with the nature and severity of the condition being treated and is of course ultimately at the discretion of the physician or veterinarian. In general, however, a suitable dose of agent will lie in the range of about 1 mg to about 200 mg per kilogram mammal body weight being treated. Administration by the parenteral route (intravenously, intradermally, intraperitoneally, intramuscularly or subcutaneously is preferred for a period of time of from 1 to 20 days.

While it is possible for the agents to be administered as the raw substances it is preferable, in view of their potency, to present them as a pharmaceutical formulation. The formulations, both veterinary and for human use, of the present invention comprise the agent, together with one or more acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier which constitutes one or more accessory ingredients. In general, the formulations are prepared by uniformly and intimately bringing into association the agent with the carrier(s) and then, if necessary, dividing the product into unit dosages thereof.

Formulations suitable for parenteral administration conveniently comprise sterile aqueous preparations of the agents which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension which is filled into a sterile container and sealed against bacterial contamination. Preferably sterile materials are used under aseptic manufacturing conditions to avoid the need for terminal sterilization.

Such formulations may optionally contain one or more additional ingredients among which may be mentioned preservatives, such as methyl hydroxybenzoate, chlorocresol, metracresol, phenol and benzalkonium chloride. Such materials are of especial value when the formulations are presented in multi-dose containers.

Buffers may also be included to provide a suitable pH value for the formulation and suitable materials include sodium phosphate and acetate. Sodium chloride or glycerin may be used to render a formulation isotonic with the blood. If desired, the formulation may be filled into the containers under an inert atmosphere such as nitrogen or may contain an antioxidant, and are conveniently presented in unit dose or multidose form, for example, in a sealed ampoule.

It will be appreciated that while the agents described herein form acid addition salts and carboxy acid salts the biological activity thereof will reside in the agent itself. These salts may be used in humans and in veterinary medicine and presented as pharmaceutical formulations in the manner and in the amounts (calculated as the base) described hereinabove, and it is then preferable that the acid moiety be pharmacologically and pharmaceutically acceptable to the recipient. Examples of such suitable acids include (a) mineral acids: hydrochloric, hydrobromic, phosphoric, metaphosphoric, and sulphuric acids; (b) organic acids: tartaric, acetic, citric, malic, lactic, fumaric, benzoic, glycollic, gluconic, gulonic, succinic and aryl-sulphonic, for example, p-toluenesulphonic acids.

Surprisingly, the compounds of the invention have also demonstrated insecticidal properties. The compounds have been found to be particularly effective against mosquitoes.

EXAMPLE 8

Mosquito eggs (1,000) were hatched at 25° C. in a cultured media consisting of well water (500 mL), baker's yeast (200 mg) and liver extract (300 mg). The eggs were maintained under these conditions for 4 to 5 days. The larvae were next transferred to test tubes containing 3 mL of culture media. Each test tube contained 10 mosquito larvae. In each experiment, 23 test tubes, each with 10 mosquitos in it, served as controls. The cidal activity of each of the polyamine analogues against the mosquito larvae was tested at, 1, 3, 10, and 30 ppm. Each compound was tested at each concentration in triplicate again in test tubes containing 10 mosquito larvae in 3 mL of culture media, maintained at 25° C. The control and test larvae were examined for insect death at 24 and 48 hour intervals. Table 9 includes representative examples of the cidal activity of the polyamine analogues against mosquito larvae. The data is reported as the $LD_{50}$ values for each compound, i.e., the concentration of polyamine required to kill 50% of the larvae. Furthermore, the data is reported at 48 and 96 hours.

TABLE 9

| Compound | 48 Hr. $LD_{50}$ | 96 Hr. $LD_{50}$ |
|---|---|---|
| $N^1,N^4$-Diethyl spermine | 2 ppm | — |
| $N^1,N^4$-Diethyl homospermine | 7 ppm | 5 ppm |

The insecticidal compounds of the invention may be dissolved or dispersed in any suitable carrier medium adapted for spraying insecticides, e.g., water or other aqueous media and sprayed on an insect infested area or areas subject to potential infestation. The concentration of polyamines applied to an area would depend on the species of insect and its accessibility, however, solutions containing from 10 to 10,000 ppm per gallon broadcast over 100 $ft^2$.

I claim:

1. A compound having the formula:

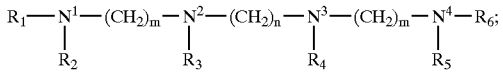

Wherein:

$R_1$–$R_6$ may be the same or different and are methyl, propyl, butyl, pentyl, benzyl or β,β,β,-trifluoro-ethyl;

m is [an integer from] 3 [to], *4, 5, or* 6[, inclusive]; *and* n is [an integer from] 3 [to], *4, 5, or* 6[, inclusive,];

or a salt thereof with an acid;

*with the proviso that if m is 3, and n is 3 or 4, then at least one of $R_1$–$R_6$ is β,β,β,-trifluoroethyl.*

2. A compound according to claim 1 wherein $R_1$ and $R_6$ are propyl.

3. A compound according to claim 1 wherein $R_1$ and $R_6$ are benzyl.

4. A compound according to claim 1 wherein m is 3 and n is 4.

5. A compound according to claim 1 wherein m and n are 3.

6. A compound according to claim 1 wherein m and n are 4.

7. A compound having the formula:

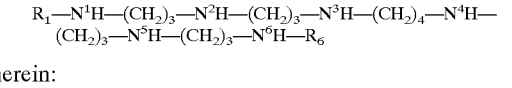

(II)

Wherein:

$R_1$ and $R_6$ may be the same or different and are alkyl or aralkyl having from 1 to 12 carbon atoms, or a salt thereof with an acid.

8. A compound according to claim 7 wherein $R_1$ and $R_6$ are alkyl.

9. A compound according to claim 7 wherein $R_1$ and $R_6$ are aralkyl.

10. A compound according to claim 7 wherein $R_1$ and $R_6$ are methyl.

11. A compound according to claim 7 wherein $R_1$ and $R_6$ are ethyl.

12. A compound according to claim 7 wherein $R_1$ and $R_6$ are propyl.

13. A compound according to claim 7 wherein $R_1$ and $R_6$ are benzyl.

14. A compound having the formula:

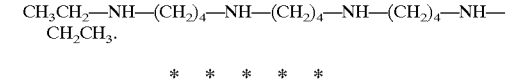

* * * * *